United States Patent [19]
Cao

[11] Patent Number: 5,776,717
[45] Date of Patent: Jul. 7, 1998

[54] IκB KINASES

[75] Inventor: Zhaodan Cao, S. San Francisco, Calif.

[73] Assignee: Tularik Inc., South San Francisco, Calif.

[21] Appl. No.: 971,937

[22] Filed: Nov. 17, 1997

Related U.S. Application Data

[62] Division of Ser. No. 812,533, Mar. 7, 1997.
[51] Int. Cl.$^6$ .............................. C12Q 1/48; C12N 9/12
[52] U.S. Cl. ............................................ 435/15; 435/194
[58] Field of Search ...................................... 435/194, 15

Primary Examiner—Robert A. Wax
Assistant Examiner—Einar Stole
Attorney, Agent, or Firm—Richard Aron Osman

[57] ABSTRACT

The invention provides methods and compositions relating to IκB regulating proteins, known as T2K proteins, and related nucleic acids. The proteins may be produced recombinantly from transformed host cells from the disclosed T2K encoding nucleic acid or purified from human cells. The invention provides specific hybridization probes and primers capable of specifically hybridizing with the disclosed T2K gene, T2K-specific binding agents such as specific antibodies, and methods of making and using the subject compositions in diagnosis, therapy and in the biopharmaceutical industry.

7 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2994 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 73..2259

( x i ) SEQUENCE DESCRIPTION: SEQ ID NO:1:

```
GCGGGAGCCC  GCCGGCGGTG  GCGCGGCGGA  GACCCGGCTG  GTATAACAAG  AGGATTGCCT                60

GATCCAGCCA  AG ATG CAG AGC ACT TCT AAT CAT CTG TGG CTT TTA TCT                      108
              Met Gln Ser Thr Ser Asn His Leu Trp Leu Leu Ser
               1               5                          10

GAT ATT TTA GGC CAA GGA GCT ACT GCA AAT GTC TTT CGT GGA AGA CAT                     156
Asp Ile Leu Gly Gln Gly Ala Thr Ala Asn Val Phe Arg Gly Arg His
         15                  20                  25

AAG AAA ACT GGT GAT TTA TTT GCT ATC AAA GTA TTT AAT AAC ATA AGC                     204
Lys Lys Thr Gly Asp Leu Phe Ala Ile Lys Val Phe Asn Asn Ile Ser
         30                  35                  40

TTC CTT CGT CCA GTG GAT GTT CAA ATG AGA GAA TTT GAA GTG TTG AAA                     252
Phe Leu Arg Pro Val Asp Val Gln Met Arg Glu Phe Glu Val Leu Lys
 45                  50                  55                  60

AAA CTC AAT CAC AAA AAT ATT GTC AAA TTA TTT GCT ATT GAA GAG GAG                     300
Lys Leu Asn His Lys Asn Ile Val Lys Leu Phe Ala Ile Glu Glu Glu
                 65                  70                  75

ACA ACA ACA AGA CAT AAA GTA CTT ATT ATG GAA TTT TGT CCA TGT GGG                     348
Thr Thr Thr Arg His Lys Val Leu Ile Met Glu Phe Cys Pro Cys Gly
                 80                  85                  90

AGT TTA TAC ACT GTT TTA GAA GAA CCT TCT AAT GCC TAT GGA CTA CCA                     396
Ser Leu Tyr Thr Val Leu Glu Glu Pro Ser Asn Ala Tyr Gly Leu Pro
             95                 100                 105

GAA TCT GAA TTC TTA ATT GTT TTG CGA GAT GTG GTG GGA GGA ATG AAT                     444
Glu Ser Glu Phe Leu Ile Val Leu Arg Asp Val Val Gly Gly Met Asn
        110                 115                 120

CAT CTA CGA GAG AAT GGT ATA GTG CAC CGT GAT ATC AAG CCA GGA AAT                     492
His Leu Arg Glu Asn Gly Ile Val His Arg Asp Ile Lys Pro Gly Asn
125                 130                 135                 140

ATC ATG CGT GTT ATA GGG GAA GAT GGA CAG TCT GTG TAC AAA CTC ACA                     540
Ile Met Arg Val Ile Gly Glu Asp Gly Gln Ser Val Tyr Lys Leu Thr
                145                 150                 155
```

-continued

| | | | | | | | | | | | | | | | | |
|---|---|---|---|---|---|---|---|---|---|---|---|---|---|---|---|---|
| GAT | TTT | GGT | GCA | GCT | AGA | GAA | TTA | GAA | GAT | GAT | GAG | CAG | TTT | GTT | TCT | 588 |
| Asp | Phe | Gly | Ala 160 | Ala | Arg | Glu | Leu 165 | Glu | Asp | Asp | Glu | Gln | Phe 170 | Val | Ser | |
| CTG | TAT | GGC | ACA | GAA | GAA | TAT | TTG | CAC | CCT | GAT | ATG | TAT | GAG | AGA | GCA | 636 |
| Leu | Tyr | Gly 175 | Thr | Glu | Glu | Tyr | Leu 180 | His | Pro | Asp | Met | Tyr 185 | Glu | Arg | Ala | |
| GTG | CTA | AGA | AAA | GAT | CAT | CAG | AAG | AAA | TAT | GGA | GCA | ACA | GTT | GAT | CTT | 684 |
| Val | Leu 190 | Arg | Lys | Asp | His | Gln 195 | Lys | Lys | Tyr | Gly | Ala 200 | Thr | Val | Asp | Leu | |
| TGG | AGC | ATT | GGG | GTA | ACA | TTT | TAC | CAT | GCA | GCT | ACT | GGA | TCA | CTG | CCA | 732 |
| Trp 205 | Ser | Ile | Gly | Val | Thr 210 | Phe | Tyr | His | Ala | Ala 215 | Thr | Gly | Ser | Leu | Pro 220 | |
| TTT | AGA | CCC | TTT | GAA | GGG | CCT | CGT | AGG | AAT | AAA | GAA | GTG | ATG | TAT | AAA | 780 |
| Phe | Arg | Pro | Phe | Glu 225 | Gly | Pro | Arg | Arg | Asn 230 | Lys | Glu | Val | Met | Tyr 235 | Lys | |
| ATA | ATT | ACA | GGA | AAG | CCT | TCT | GGT | GCA | ATA | TCT | GGA | GTA | CAG | AAA | GCA | 828 |
| Ile | Ile | Thr | Gly 240 | Lys | Pro | Ser | Gly | Ala 245 | Ile | Ser | Gly | Val | Gln 250 | Lys | Ala | |
| GAA | AAT | GGA | CCA | ATT | GAC | TGG | AGT | GGA | GAC | ATG | CCT | GTT | TCT | TGC | AGT | 876 |
| Glu | Asn | Gly 255 | Pro | Ile | Asp | Trp | Ser 260 | Gly | Asp | Met | Pro | Val 265 | Ser | Cys | Ser | |
| CTT | TCT | CGG | GGT | CTT | CAG | GTT | CTA | CTT | ACC | CCT | GTT | CTT | GCA | AAC | ATC | 924 |
| Leu | Ser 270 | Arg | Gly | Leu | Gln | Val 275 | Leu | Leu | Thr | Pro | Val 280 | Leu | Ala | Asn | Ile | |
| CTT | GAA | GCA | GAT | CAG | GAA | AAG | TGT | TGG | GGT | TTT | GAC | CAG | TTT | TTT | GCA | 972 |
| Leu 285 | Glu | Ala | Asp | Gln | Glu 290 | Lys | Cys | Trp | Gly | Phe 295 | Asp | Gln | Phe | Phe | Ala 300 | |
| GAA | ACT | AGT | GAT | ATA | CTT | CAC | CGA | ATG | GTA | ATT | CAT | GTT | TTT | TCG | CTA | 1020 |
| Glu | Thr | Ser | Asp | Ile 305 | Leu | His | Arg | Met | Val 310 | Ile | His | Val | Phe | Ser 315 | Leu | |
| CAA | CAA | ATG | ACA | GCT | CAT | AAG | ATT | TAT | ATA | CAT | AGC | TAT | AAT | ACT | GCT | 1068 |
| Gln | Gln | Met | Thr 320 | Ala | His | Lys | Ile | Tyr 325 | Ile | His | Ser | Tyr | Asn 330 | Thr | Ala | |
| ACT | ATA | TTT | CAT | GAA | CTG | GTA | TAT | AAA | CAA | ACC | AAA | ATT | ATT | TCT | TCA | 1116 |
| Thr | Ile | Phe 335 | His | Glu | Leu | Val | Tyr 340 | Lys | Gln | Thr | Lys | Ile 345 | Ile | Ser | Ser | |
| AAT | CAA | GAA | CTT | ATC | TAC | GAA | GGG | CGA | CGC | TTA | GTC | TTA | GAA | CCT | GGA | 1164 |
| Asn | Gln | Glu 350 | Leu | Ile | Tyr | Glu | Gly 355 | Arg | Arg | Leu | Val | Leu 360 | Glu | Pro | Gly | |
| AGG | CTG | GCA | CAA | CAT | TTC | CCT | AAA | ACT | ACT | GAG | GAA | AAC | CCT | ATA | TTT | 1212 |
| Arg 365 | Leu | Ala | Gln | His | Phe 370 | Pro | Lys | Thr | Thr | Glu 375 | Glu | Asn | Pro | Ile | Phe 380 | |
| GTA | GTA | AGC | CGG | GAA | CCT | CTG | AAT | ACC | ATA | GGA | TTA | ATA | TAT | GAA | AAA | 1260 |
| Val | Val | Ser | Arg | Glu 385 | Pro | Leu | Asn | Thr | Ile 390 | Gly | Leu | Ile | Tyr | Glu 395 | Lys | |
| ATT | TCC | CTC | CCT | AAA | GTA | CAT | CCA | CGT | TAT | GAT | TTA | GAC | GGG | GAT | GCT | 1308 |
| Ile | Ser | Leu | Pro 400 | Lys | Val | His | Pro 405 | Arg | Tyr | Asp | Leu | Asp 410 | Gly | Asp | Ala | |
| AGC | ATG | GCT | AAG | GCA | ATA | ACA | GGG | GTT | GTG | TGT | TAT | GCC | TGC | AGA | ATT | 1356 |
| Ser | Met | Ala 415 | Lys | Ala | Ile | Thr | Gly 420 | Val | Val | Cys | Tyr | Ala 425 | Cys | Arg | Ile | |
| GCC | AGT | ACC | TTA | CTG | CTT | TAT | CAG | GAA | TTA | ATG | CGA | AAG | GGG | ATA | CGA | 1404 |
| Ala | Ser | Thr 430 | Leu | Leu | Leu | Tyr | Gln 435 | Glu | Leu | Met | Arg | Lys 440 | Gly | Ile | Arg | |
| TGG | CTG | ATT | GAA | TTA | ATT | AAA | GAT | GAT | TAC | AAT | GAA | ACT | GTT | CAC | AAA | 1452 |
| Trp 445 | Leu | Ile | Glu | Leu | Ile 450 | Lys | Asp | Asp | Tyr | Asn 455 | Glu | Thr | Val | His | Lys 460 | |
| AAG | ACA | GAA | GTT | GTG | ATC | ACA | TTG | GAT | TTC | TGT | ATC | AGA | AAC | ATT | GAA | 1500 |
| Lys | Thr | Glu | Val | Val 465 | Ile | Thr | Leu | Asp | Phe 470 | Cys | Ile | Arg | Asn | Ile 475 | Glu | |

```
AAA ACT GTG AAA GTA TAT GAA AAG TTG ATG AAG ATC AAC CTG GAA GCG         1548
Lys Thr Val Lys Val Tyr Glu Lys Leu Met Lys Ile Asn Leu Glu Ala
        480             485                 490

GCA GAG TTA GGT GAA ATT TCA GAC ATA CAC ACC AAA TTG TTG AGA CTT         1596
Ala Glu Leu Gly Glu Ile Ser Asp Ile His Thr Lys Leu Leu Arg Leu
            495             500             505

TCC AGT TCT CAG GGA ACA ATA GAA ACC AGT CTT CAG GAT ATC GAC AGC         1644
Ser Ser Ser Gln Gly Thr Ile Glu Thr Ser Leu Gln Asp Ile Asp Ser
    510                 515             520

AGA TTA TCT CCA GGT GGA TCA CTG GCA GAC GCA TGG GCA CAT CAA GAA         1692
Arg Leu Ser Pro Gly Gly Ser Leu Ala Asp Ala Trp Ala His Gln Glu
525                 530             535                 540

GGC ACT CAT CCG AAA GAC AGA AAT GTA GAA AAA CTA CAA GTC CTG TTA         1740
Gly Thr His Pro Lys Asp Arg Asn Val Glu Lys Leu Gln Val Leu Leu
            545             550             555

AAT TGC ATG ACA GAG ATT TAC TAT CAG TTC AAA AAA GAC AAA GCA GAA         1788
Asn Cys Met Thr Glu Ile Tyr Tyr Gln Phe Lys Lys Asp Lys Ala Glu
            560             565             570

CGT AGA TTA GCT TAT AAT GAA GAA CAA ATC CAC AAA TTT GAT AAG CAA         1836
Arg Arg Leu Ala Tyr Asn Glu Glu Gln Ile His Lys Phe Asp Lys Gln
            575             580             585

AAA CTG TAT TAC CAT GCC ACA AAA GCT ATG ACG CAC TTT ACA GAT GAA         1884
Lys Leu Tyr Tyr His Ala Thr Lys Ala Met Thr His Phe Thr Asp Glu
    590             595             600

TGT GTT AAA AAG TAT GAG GCA TTT TTG AAT AAG TCA GAA GAA TGG ATA         1932
Cys Val Lys Lys Tyr Glu Ala Phe Leu Asn Lys Ser Glu Glu Trp Ile
605             610             615                 620

AGA AAG ATG CTT CAT CTT AGG AAA CAG TTA TTA TCG CTG ACT AAT CAG         1980
Arg Lys Met Leu His Leu Arg Lys Gln Leu Leu Ser Leu Thr Asn Gln
            625             630             635

TGT TTT GAT ATT GAA GAA GAA GTA TCA AAA TAT CAA GAA TAT ACT AAT         2028
Cys Phe Asp Ile Glu Glu Glu Val Ser Lys Tyr Gln Glu Tyr Thr Asn
            640             645             650

GAG TTA CAA GAA ACT CTG CCT CAG AAA ATG TTT ACA GCT TCC AGT GGA         2076
Glu Leu Gln Glu Thr Leu Pro Gln Lys Met Phe Thr Ala Ser Ser Gly
        655             660             665

ATC AAA CAT ACC ATG ACC CCA ATT TAT CCA AGT TCT AAC ACA TTA GTA         2124
Ile Lys His Thr Met Thr Pro Ile Tyr Pro Ser Ser Asn Thr Leu Val
        670             675             680

GAA ATG ACT CTT GGT ATG AAG AAA TTA AAG GAA GAG ATG GAA GGG GTG         2172
Glu Met Thr Leu Gly Met Lys Lys Leu Lys Glu Glu Met Glu Gly Val
685             690             695             700

GTT AAA GAA CTT GCT GAA AAT AAC CAC ATT TTA GAA AGG TTT GGC TCT         2220
Val Lys Glu Leu Ala Glu Asn Asn His Ile Leu Glu Arg Phe Gly Ser
                705             710             715

TTA ACC ATG GAT GGT GGC CTT CGC AAC GTT GAC TGT CTT TAGCTTTCTA         2269
Leu Thr Met Asp Gly Gly Leu Arg Asn Val Asp Cys Leu
            720             725

ATAGAAGTTT AAGAAAAGTT TCCGTTTGCA CAAGAAAATA ACGCTTGGGC ATTAAATGAA       2329

TGCCTTTATA GATAGTCACT TGTTTCTACA ATTCAGTATT TGATGTGGTC GTGTAAATAT       2389

GTACAATATT GTAAATACAT AAAAAATATA CAAATTTTTG GCTGCTGTGA AATGTAATT        2449

TTATCTTTTA ACATTTATAA TTATATGAGG AAATTTGACC TCAGTGATCA CGAGAAGAAA       2509

GCCATGACCG ACCAATATGT TGACATACTG ATCCTCTACT CTGAGTGGGG CTAAATAAGT       2569

TATTTCTCT GACCGCCTAC TGGAAATATT TTAAGTGGA ACCAAAATAG GCATCCTTAC         2629

AAATCAGGAA GACTGACTTG ACACGTTTGT AAATGGTAGA ACGGTGGCTA CTGTGAGTGG       2689

GGAGCAGAAC CGCACCACTG TTATACTGGG ATAACAATTT TTTGAGAAG GATAAAGTGG       2749
```

| | | | | | |
|---|---|---|---|---|---|
| CATTATTTTA | TTTTACAAGG | TGCCCAGATC | CCAGTTATCC | TTGTATCCAT | GTAATTTCAG | 2809 |
| ATGAATTATT | AAGCAAACAT | TTTAAAGTGA | ATTCATTATT | AAAAACTATT | CATTTTTTC | 2869 |
| CTTTGGCCAT | AAATGTGTAA | TTGTCATTAA | AATTCTAAGG | TCATTTCAAC | TGTTTTAAGC | 2929 |
| TGTATTTCTT | TAATTCTGCT | TACTATTTCA | TGGAAAAAAA | TAAATTTCTC | AATTTTAAAA | 2989 |
| AAAAA | | | | | | 2994 |

(2) INFORMATION FOR SEQ ID NO:2:

(i) SEQUENCE CHARACTERISTICS:
        (A) LENGTH: 729 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Ser Thr Ser Asn His Leu Trp Leu Ser Asp Ile Leu Gly
 1               5                  10                  15

Gln Gly Ala Thr Ala Asn Val Phe Arg Gly Arg His Lys Lys Thr Gly
                20                  25                  30

Asp Leu Phe Ala Ile Lys Val Phe Asn Asn Ile Ser Phe Leu Arg Pro
            35                  40                  45

Val Asp Val Gln Met Arg Glu Phe Glu Val Leu Lys Lys Leu Asn His
    50                  55                  60

Lys Asn Ile Val Lys Leu Phe Ala Ile Glu Glu Thr Thr Thr Arg
65                  70                  75                  80

His Lys Val Leu Ile Met Glu Phe Cys Pro Cys Gly Ser Leu Tyr Thr
                85                  90                  95

Val Leu Glu Glu Pro Ser Asn Ala Tyr Gly Leu Pro Glu Ser Glu Phe
            100                 105                 110

Leu Ile Val Leu Arg Asp Val Val Gly Gly Met Asn His Leu Arg Glu
        115                 120                 125

Asn Gly Ile Val His Arg Asp Ile Lys Pro Gly Asn Ile Met Arg Val
    130                 135                 140

Ile Gly Glu Asp Gly Gln Ser Val Tyr Lys Leu Thr Asp Phe Gly Ala
145                 150                 155                 160

Ala Arg Glu Leu Glu Asp Asp Glu Gln Phe Val Ser Leu Tyr Gly Thr
                165                 170                 175

Glu Glu Tyr Leu His Pro Asp Met Tyr Glu Arg Ala Val Leu Arg Lys
            180                 185                 190

Asp His Gln Lys Lys Tyr Gly Ala Thr Val Asp Leu Trp Ser Ile Gly
        195                 200                 205

Val Thr Phe Tyr His Ala Ala Thr Gly Ser Leu Pro Phe Arg Pro Phe
    210                 215                 220

Glu Gly Pro Arg Arg Asn Lys Glu Val Met Tyr Lys Ile Ile Thr Gly
225                 230                 235                 240

Lys Pro Ser Gly Ala Ile Ser Gly Val Gln Lys Ala Glu Asn Gly Pro
                245                 250                 255

Ile Asp Trp Ser Gly Asp Met Pro Val Ser Cys Ser Leu Ser Arg Gly
            260                 265                 270

Leu Gln Val Leu Leu Thr Pro Val Leu Ala Asn Ile Leu Glu Ala Asp
        275                 280                 285

Gln Glu Lys Cys Trp Gly Phe Asp Gln Phe Phe Ala Glu Thr Ser Asp
    290                 295                 300

Ile Leu His Arg Met Val Ile His Val Phe Ser Leu Gln Gln Met Thr
```

-continued

| 305 | | | | | | | 310 | | | | | | | 315 | | | | | | 320 |
|---|---|---|---|---|---|---|---|---|---|---|---|---|---|---|---|---|---|---|---|---|
| Ala | His | Lys | Ile | Tyr | Ile | His | Ser | Tyr | Asn | Thr | Ala | Thr | Ile | Phe | His |
| | | | | 325 | | | | | 330 | | | | | 335 | |
| Glu | Leu | Val | Tyr | Lys | Gln | Thr | Lys | Ile | Ile | Ser | Ser | Asn | Gln | Glu | Leu |
| | | | | 340 | | | | | 345 | | | | | 350 | |
| Ile | Tyr | Glu | Gly | Arg | Arg | Leu | Val | Leu | Glu | Pro | Gly | Arg | Leu | Ala | Gln |
| | | | 355 | | | | | 360 | | | | 365 | | | |
| His | Phe | Pro | Lys | Thr | Thr | Glu | Glu | Asn | Pro | Ile | Phe | Val | Val | Ser | Arg |
| | | 370 | | | | | 375 | | | | | 380 | | | |
| Glu | Pro | Leu | Asn | Thr | Ile | Gly | Leu | Ile | Tyr | Glu | Lys | Ile | Ser | Leu | Pro |
| 385 | | | | | | 390 | | | | | 395 | | | | 400 |
| Lys | Val | His | Pro | Arg | Tyr | Asp | Leu | Asp | Gly | Asp | Ala | Ser | Met | Ala | Lys |
| | | | | 405 | | | | | 410 | | | | | 415 | |
| Ala | Ile | Thr | Gly | Val | Val | Cys | Tyr | Ala | Cys | Arg | Ile | Ala | Ser | Thr | Leu |
| | | | 420 | | | | | 425 | | | | | 430 | | |
| Leu | Leu | Tyr | Gln | Glu | Leu | Met | Arg | Lys | Gly | Ile | Arg | Trp | Leu | Ile | Glu |
| | | 435 | | | | | 440 | | | | | 445 | | | |
| Leu | Ile | Lys | Asp | Asp | Tyr | Asn | Glu | Thr | Val | His | Lys | Lys | Thr | Glu | Val |
| | 450 | | | | | 455 | | | | | 460 | | | | |
| Val | Ile | Thr | Leu | Asp | Phe | Cys | Ile | Arg | Asn | Ile | Glu | Lys | Thr | Val | Lys |
| 465 | | | | | 470 | | | | | 475 | | | | | 480 |
| Val | Tyr | Glu | Lys | Leu | Met | Lys | Ile | Asn | Leu | Glu | Ala | Ala | Glu | Leu | Gly |
| | | | | 485 | | | | | 490 | | | | | 495 | |
| Glu | Ile | Ser | Asp | Ile | His | Thr | Lys | Leu | Leu | Arg | Leu | Ser | Ser | Ser | Gln |
| | | | 500 | | | | | 505 | | | | | 510 | | |
| Gly | Thr | Ile | Glu | Thr | Ser | Leu | Gln | Asp | Ile | Asp | Ser | Arg | Leu | Ser | Pro |
| | | | 515 | | | | | 520 | | | | | 525 | | |
| Gly | Gly | Ser | Leu | Ala | Asp | Ala | Trp | Ala | His | Gln | Glu | Gly | Thr | His | Pro |
| | | 530 | | | | 535 | | | | | 540 | | | | |
| Lys | Asp | Arg | Asn | Val | Glu | Lys | Leu | Gln | Val | Leu | Leu | Asn | Cys | Met | Thr |
| 545 | | | | | 550 | | | | | 555 | | | | | 560 |
| Glu | Ile | Tyr | Tyr | Gln | Phe | Lys | Lys | Asp | Lys | Ala | Glu | Arg | Arg | Leu | Ala |
| | | | | 565 | | | | | 570 | | | | | 575 | |
| Tyr | Asn | Glu | Glu | Gln | Ile | His | Lys | Phe | Asp | Lys | Gln | Lys | Leu | Tyr | Tyr |
| | | | 580 | | | | | 585 | | | | | 590 | | |
| His | Ala | Thr | Lys | Ala | Met | Thr | His | Phe | Thr | Asp | Glu | Cys | Val | Lys | Lys |
| | | 595 | | | | | 600 | | | | | 605 | | | |
| Tyr | Glu | Ala | Phe | Leu | Asn | Lys | Ser | Glu | Glu | Trp | Ile | Arg | Lys | Met | Leu |
| | 610 | | | | | 615 | | | | | 620 | | | | |
| His | Leu | Arg | Lys | Gln | Leu | Leu | Ser | Leu | Thr | Asn | Gln | Cys | Phe | Asp | Ile |
| 625 | | | | | 630 | | | | | 635 | | | | | 640 |
| Glu | Glu | Glu | Val | Ser | Lys | Tyr | Gln | Glu | Tyr | Thr | Asn | Glu | Leu | Gln | Glu |
| | | | | 645 | | | | | 650 | | | | | 655 | |
| Thr | Leu | Pro | Gln | Lys | Met | Phe | Thr | Ala | Ser | Ser | Gly | Ile | Lys | His | Thr |
| | | | 660 | | | | | 665 | | | | | 670 | | |
| Met | Thr | Pro | Ile | Tyr | Pro | Ser | Ser | Asn | Thr | Leu | Val | Glu | Met | Thr | Leu |
| | | 675 | | | | | 680 | | | | | 685 | | | |
| Gly | Met | Lys | Lys | Leu | Lys | Glu | Glu | Met | Glu | Gly | Val | Val | Lys | Glu | Leu |
| | | 690 | | | | | 695 | | | | | 700 | | | |
| Ala | Glu | Asn | Asn | His | Ile | Leu | Glu | Arg | Phe | Gly | Ser | Leu | Thr | Met | Asp |
| 705 | | | | | 710 | | | | | 715 | | | | | 720 |
| Gly | Gly | Leu | Arg | Asn | Val | Asp | Cys | Leu | | | | | | | |
| | | | | 725 | | | | | | | | | | | |

IκB KINASES

This is a division of application Ser. No. 08/812,533 filed Mar. 7, 1997.

FIELD OF THE INVENTION

The field of this invention is a family of kinases which regulate signal transduction.

BACKGROUND

Inflammatory cytokines IL-1 and TNF exert diverse biological activities by altering gene expression in the cells, a function mediated mostly by transcription factor NF-κB. In unstimulated cells, NF-κB proteins form a complex with inhibitory molecules, the IκB proteins, and are rendered inactive in the cytoplasm. In response to cytokines and other stimuli, the IκB proteins are phosphorylated on specific serine residues. In particular, phosphorylation of two serine residues as part of the consensus sequence DSGL/IXSM/L (e.g. ser 32 and 36 in IκBα, ser 19 and 23 in IκBβ, and ser 157 and 161, or 18 and 22, depending on the usage of methionines, in IκBE, respectively) which mark the proteins for ubiquitination and proteosome-mediated degradation, releasing NF-κB to enter the nucleus to activate the genes that encode proteins participating in inflammatory and immune responses. Henceforth, the term IκB serine 36 is used herein to refer generically to the second serine residue of the foregoing consensus sequence, e.g. that corresponding to serine 36 in IκBα, ser 23 in IκKβ, and ser 161 or 22 in IκBε.

Delineating TNF and IL-1 signaling pathways for NF-κB activation has implicated the TRAF molecules as converging point for different cytokines, with TRAF2 being involved in TNF- and TRAF6.in IL-1-induced NF-KB activation. We disclose herein a family of IκB kinases including a TRAF2-associated kinase activity (designated T2K) and the translation product of the KIAA0151 gene product that phosphorylates the IKB molecules on the specific regulatory serine residues. We also disclose the purification of a native protein responsible for such kinase activity, the sequencing of T2K peptides derived, and the cloning of native T2K cDNA.

Nagase et al. (1995) DNA Res. 2(4),167–174 report conceptual coding sequences from a number of unidentified human genes including KIAA0151. Song et al., U.S. patent application Ser. No. 08/677,862 discloses a TRAF2-associated kinase.

SUMMARY OF THE INVENTION

The invention provides methods and compositions relating to natural isolated regulatory proteins called T2K proteins, related nucleic acids, and protein domains thereof having T2K-specific activity. The proteins may be produced recombinantly from transformed host cells from the subject T2K encoding nucleic acids or purified from mammalian cells. The invention provides isolated T2K hybridization probes and primers capable of specifically hybridizing with the disclosed T2K gene, T2K-specific binding agents such as specific antibodies, and methods of making and using the subject compositions in diagnosis (e.g. genetic hybridization screens for T2K transcripts), therapy (e.g. gene therapy to modulate T2K gene expression) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequences of a natural cDNA encoding a human T2K protein is shown as SEQ ID NO: 1, and the full conceptual translate is shown as SEQ ID NO:2. The T2K proteins of the invention include incomplete translates of SEQ ID NO: I and deletion mutants of SEQ ID NO:2, which translates and deletion mutants have T2K-specific amino acid sequence and assay-discernable T2K-specific binding specificity or function. Such active T2K deletion mutants, T2K peptides or protein domains comprise a sequence of at least about 6, preferably at least about 8, more preferably at least about 10 consecutive residues of SEQ ID NO:2 which distinguishes both the KIAA0151 gene product and the translation product of SEQ ID NO: 1, bases 1756–2095. For examples, T2K protein domains identified below are shown to provide protein-binding domains which are identified in and find use, inter alia, in solid-phase binding and kinase assays as described below.

T2K-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an T2K protein with a binding target is evaluated. The binding target may be a natural intracellular binding target (including substrates, agonists and antagonists) such as an IκB or TRAF2, or other regulator that directly modulates T2K activity or its localization; or non-natural binding target such a specific immune protein such as an antibody, or an T2K specific agent such as those identified in screening assays such as described below. T2K-binding specificity may assayed by binding equilibrium constants (usually at least about $10^7$ $M^{-1}$, preferably at least about $10^8$ $M^{-1}$, more preferably at least about $10^9$ $M^{-1}$), by the ability of the subject protein to function as negative mutants in T2K-expressing cells, to elicit T2K specific antibody in a heterologous host (e.g. a rodent or rabbit), etc.; or, in a preferred embodiment, by kinase activity.

The claimed T2K proteins are isolated or pure: an "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. The T2K proteins and protein domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides natural and non-natural T2K-specific binding agents, methods of identifying and making such agents, and their use in diagnosis, therapy and pharmaceutical development. For example, T2K-specific agents are useful in a variety of diagnostic and therapeutic applications. Novel T2K-specific binding agents include T2K-specific receptors, such as somatically recombined protein receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. For diagnostic uses, the binding agents are frequently labeled, such as with fluorescent, radioactive, chemiluminescent, or other easily detectable molecules, either conjugated directly to the binding agent or conjugated to a probe specific for the binding agent. Agents of particular interest modulate T2K function, e.g. T2K kinase activity; for example, isolated cells, whole tissues, or individuals may be treated with a T2K binding agent to activate, inhibit, or alter T2K-kinase dependent processes such as NfκB activation.

The amino acid sequences of the disclosed T2K proteins are used to back-translate T2K protein-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural T2K-encoding nucleic acid sequences ("GCG" software, Genetics Computer Group, Inc. Madison Wis.). T2K-encoding nucleic acids used in T2K-expression vectors and incorporated into recombinant host cells, e.g. for expression and screening, transgenic animals, e.g. for functional studies such as the efficacy of candidate drugs for disease associated with T2K-modulated cell function, etc.

The invention also provides nucleic acid hybridization probes and replication/amplification primers having a hitherto novel T2K cDNA specific sequence contained in SEQ ID NO: 1 (including its complement and analogs and complements thereof having the corresponding sequence, e.g. in RNA) and sufficient to effect specific hybridization thereto (i.e. specifically hybridize with SEQ ID NO: 1 in the presence of the KIAAO 151 gene and nucleic acids consisting of SEQ ID NO: 1, bases 1756–2095). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18M NaCl, 0.01 M NaPO$_4$, pH7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. T2K cDNA homologs can also be distinguished from other protein using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO: 1 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of T2K genes and gene transcripts and in detecting or amplifying nucleic acids encoding additional T2K homologs and structural analogs. In diagnosis, T2K hybridization probes find use in identifying wild-type and mutant T2K alleles in clinical and laboratory samples. Mutant alleles are used to generate allele-specific oligonucleotide (ASO) probes for high-throughput clinical diagnoses. In therapy, therapeutic T2K nucleic acids are used to modulate cellular expression or intracellular concentration or availability of active T2K. For example, T2K nucleic acids are also used to modulate cellular expression or intracellular concentration or availability of active T2K protein. T2K inhibitory nucleic acids are typically antisense: single-stranded sequences comprising complements of the disclosed natural T2K coding sequences. Antisense modulation of the expression of a given T2K protein may employ antisense nucleic acids operably linked to gene regulatory sequences. Cell are transfected with a vector comprising a T2K sequence with a promoter sequence oriented such that transcription of the gene yields an antisense transcript capable of binding to endogenous T2K encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given T2K protein may be administered to the target cell, in or temporarily isolated from a host, at a concentration that results in a substantial reduction in expression of the targeted protein. An enhancement in T2K expression is effected by introducing into the targeted cell type T2K nucleic acids which increase the functional expression of the corresponding gene products. Such nucleic acids may be T2K expression vectors, vectors which upregulate the functional expression of an endogenous allele, or replacement vectors for targeted correction of mutant alleles. Techniques for introducing the nucleic acids into viable cells are known in the art and include retroviral-based transfection, viral coat protein-liposome mediated transfection, etc.

The invention provides efficient methods of identifying agents, compounds or lead compounds for agents active at the level of an IKB serine 36 specific kinase protein modulatable cellular function. Generally, these screening methods involve assaying for compounds which modulate IKB serine 36 specific kinase protein interaction with a natural IκB serine 36 specific kinase protein binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Such libraries encompass candidate agents of encompass numerous chemical classes, though typically they are organic compounds; preferably small organic compounds and are obtained from a wide variety of sources including libraries of synthetic or natural compounds. Identified agents find use in the pharmaceutical industries for animal and human trials; for example, the agents may be derivatized and rescreened in in vitro and in vivo assays to optimize activity and minimize toxicity for pharmaceutical development.

In vitro binding assays employ a mixture of components including a IκB serine 36 specific kinase protein such as a T2K protein, which may be part of a fusion product with another peptide or polypeptide, e.g. a tag for detection or anchoring, etc. The assay mixtures comprise a natural intracellular binding target of the kinase protein. While native binding targets may be used, it is frequently preferred to use portions (e.g. peptides) thereof so long as the portion provides binding affinity and avidity to the subject kinase protein conveniently measurable in the assay. In a particular embodiment, the binding target is a substrate comprising IκB serine 36. Such substrates comprise a IκBα, β or ε peptide including the serine 36 residue and at least 5, preferably at least 10, and more preferably at least 20 naturally occuring immediately flanking residues on each side (i.e. residues 26–46, 22–42, or 12–32 or 151–171 for IκBα, β or ε-derived substrates, respectively).

The assay mixture also comprises a candidate pharmacological agent and typically, a variety of other reagents such as salts, buffers, neutral proteins, e.g. albumin, detergents, protease inhibitors, nuclease inhibitors, antimicrobial agents, etc. The mixture components can be added in any order that provides for the requisite bindings and incubations may be performed at any temperature which facilitates optimal binding. The mixture is then incubated under conditions whereby, but for the presence of the candidate pharmacological agent, the kinase protein specifically binds the cellular binding target, portion or analog with a reference binding affinity. Incubation periods are likewise selected for optimal binding but also minimized to facilitate rapid, high-throughput screening.

After incubation, the agent-biased binding between the kinase protein and one or more binding targets is detected by any convenient way. First, a separation step is generally used to separate bound from unbound components. Separation may be effected by precipitation (e.g. TCA precipitation, immunoprecipitation, etc.), immobilization (e.g on a solid substrate), etc., followed by washing by, for examples, membrane filtration, gel chromatography (e.g. gel filtration, affinity, etc.). One of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc. A difference in the binding affinity of the kinase protein to the target in the absence of the agent as compared with the binding affinity in the presence of the agent indicates that the agent modulates the binding of the kinase protein to the binding target. Analogously, in the cell-based transcription assay also described below, a difference in the kinase protein transcriptional induction in the presence and absence of an agent indicates the agent modulates kinase-modulated transcription. A difference, as used herein, is statistically significant and preferably represents at least a 50%, more preferably at least a 90% difference.

The following experimental section and examples are offered by way of illustration and not by way of limitation.

EXPERIMENTAL

Identification of T2K:

293 cells were stably transfected with DNA plasmids that direct the expression of the human TRAF2 protein with an N-terminal Flag-epitope tag. Cells grown in suspension culture were pelleted in 500 ml bottles in a Sorvall GS-3 rotor spun at 2000 RPM for 5 minutes and were lysed in 5 pelleted-cell-volumes of "lysis buffer" containing 50 mM Hepes, pH 7.9, 250 mM NaCl, 5 mM dithiothreitol (DTT), 1 mM EDTA, 20 mM β glycerophosphate, 5 mM p-nitrophenyl phosphate, 1 mM Na orthovanadate, 1 mM benzamidine, 0.4 mM phenylmethylsulfonyl fluoride (PMSF), 1 mM Na metabisulfite, 0.1% NP-40 and 10% (v/v) glycerol. After incubation on ice for 30 minutes with occasional rocking, cell lysate was centrifuged in a 50 ml conical tube in a Sorvall H6000A rotor at 4000 RPM for 10 minutes. Supernatants were collected and centrifuged in a Beckman 45 TI rotor at 40,000 RPM for 2 hours. The TRAF complex was immunoprecipitated using anti-flag monoclonal antibodies cross-linked to sepharose (VWR) (1.5 ml sepharose beads for 200 mls of extracts). The immunoprecipitates were washed 4 times with cell lysis buffer, twice with lysis buffer containing 1 molar NaCl, then twice with lysis buffer. At this stage, the immunocomplex can efficiently phosphorylate wild type IκBα and β but not the mutants with the two serines substituted with alanines. The sepharose beads containing TRAF2 complex were then incubated at 30° C. for 1 hour in 4.5 mls of kinase buffer containing 20 mM Tris-HCl pH 7.6, 20 mM MgCl$_2$, 20 mM β glycerophosphate, 20 mM p-nitrophenyl phosphate, 1 mM EDTA, 1 mM Na orthovanadate, 1 mM benzamidine, 0.4 mM PMSF, 1 mM Na metabisulfite, 1 mM ATP, and 20 mM creatinephosphate. After the in vitro kinase reaction, significant amounts of the IκB kinase activity were found in the soluble fraction which was loaded on an 1 ml heparin agarose column and eluted with a NaCl gradient. The IKB kinase activity was recovered in the flow though fraction which was concentrated with a centricon (Amicon) to 50 ul. The material was fractionated on a superdex 200 gel filtration column driven by the Smart system (Pharmacia) and the eluate was collected in 50 ul fractions. The kinase activity was recovered in the fractions that correlated with molecule size marker of 670 kD. These fractions were pooled and further separated on a Mono Q column by a NaCl linear gradient. The kinase activity was found in 0.3 to 0.4M NaCl eluate. Silver staining of the column fractions separated on SDS gels revealed an 85 to 90 kD polypeptide that correlated with the kinase activity in both superdex 200 and Mono Q fractionation. After SDS gel separation, this polypeptide was subjected to micropeptide sequencing. One peptide sequence obtained matched a partial cDNA sequence in the Merck-Washington University Est database. A cDNA clone that contains open reading frame for 729 amino acids was isolated from a lambda phage cDNA library generated from HeLa cells. Sequence analysis revealed a protein kinase domain in the N-terminal portion of the predicted protein (T2K). Searching protein sequence database with the kinase domain of T2K identified a protein (KIAAO151) highly homologous to T2K, specially in the protein kinase domain (75% identity). KIAA0151 is a kinase with undefined function and was reported by Nagase T. et al. as a novel cDNA sequence isolated from human KG-1 cells (DNA Res. 2 (4), 167–174 (1995).

Substrate specificity analysis revealed that both T2K and KIAA0151 specifically phosphorylate IκB serine 36 and associate with TRAF2. Furthermore, deletion mutant analysis reveals that residues 10–250 define kinase domains and residues 251–729 and 251–716, for T2K and KIAA0151 respectively, define regulatory domains active as a negative mutants for IκB kinase activity. Recombinant T2K kinase is prepared by over-expressing GST fusion proteins in E. coli and baculavirus expression systems.

EXAMPLES

1. Protocol for at T2K-IκBα phosphorylation assay.
   A. Reagents:

Neutralite Avidin: 20 μg/ml in PBS.

kinase: $10^{-8}$–$10^{-5}$M kinase (SEQ ID NO:2) at 20 μg/ml in PBS.

substrate: $10^{-7}$–$10^{-4}$M biotinylated substrate (21 residue peptide consisting of residues 26–46 of human IκBα) at 40 μg/ml in PBS.

Blocking buffer: 5% BSA, 0.5% Tween 20 in PBS; 1 hour at room temperature.

Assay Buffer: 100 mM KCl, 10 mM $MgCl_2$, 1 mM $MnCl_2$, 20 mM HEPES pH 7.4, 0.25 mM EDTA, 1% glycerol, 0.5% NP-40, 50 mM BME, 1 mg/ml BSA, cocktail of protease inhibitors.

$[^{32}P]\gamma$-ATP 10×stock: $2\times10^{-5}$M cold ATP with 100 μCi $[^{32}P]\gamma$-ATP. Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2mM $NaVo_3$ (Sigma # S-6508) in 10 ml of PBS.

B. Preparation of assay plates:

Coat with 120 μl of stock N Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 40 μl biotinylated substrate (2–200 pmoles/40 ul in assay buffer)

Add 40 μl kinase (0.1–10 pmoles/40 ul in assay buffer)

Add 10 μl compound or extract.

Add 10 μl $[^{32}P]\gamma$-ATP 10×stock.

Shake at 25° C. for 15 minutes.

Incubate additional 45 minutes at 25° C.

Stop the reaction by washing 4 times with 200 μl PBS.

Add 150 μl scintillation cocktail.

Count in Topcount.

D. Controls for all assays (located on each plate):
   a. Non-specific binding
   b. cold ATP at 80% inhibition.

2. Protocol for at KIAA0151-IκBβ phosphorylation assay.
   A. Reagents:

Neutralite Avidin: 20 μg/ml in PBS.

kinase: $10^{-8}$–$10^{-5}$M truncated KIAA0151 kinase (residues 4–714) at 20 μg/ml in PBS.

substrate: $10^{-7}$–$10^{-4}$M biotinylated substrate (21 residue peptide consisting of residues 22–42 of human IκBβ) at 40 μg/ml in PBS.

Blocking buffer: 5% BSA, 0.5% Tween 20 in PBS; 1 hour at room temperature.

Assay Buffer: 100 mM KCl, 10 mM $MgCl_2$, 1 mM $MnCl_2$, 20 mM HEPES pH 7.4, 0.25 mM EDTA, 1% glycerol, 0.5% NP-40, 50 mM BME, 1 mg/ml BSA, cocktail of protease inhibitors.

-$[^{32}P]\gamma$-ATP 10×stock: $2\times10^{-5}$M cold ATP with 100 μCi $[^{32}P]\Delta$-ATP. Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2mM $NaVo_3$ (Sigma # S-6508) in 10 ml of PBS.

B. Preparation of assay plates:

Coat with 120 μl of stock N Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 40 μl biotinylated substrate (2–200 pmoles/40 ul in assay buffer)

Add 40 μl kinase (0.1–10 pmoles/40 ul in assay buffer)

Add 40 μl compound or extract.

Add 10 μl $[^{32}P]\gamma$-ATP 10×stock.

Shake at 25° C. for 15 minutes.

Incubate additional 45 minutes at 25° C.

Stop the reaction by washing 4 times with 200 μl PBS.

Add 150 μl scintillation cocktail.

Count in Topcount.

D. Controls for all assays (located on each plate):
   a. Non-specific binding
   b. cold ATP at 80% inhibition.

3. Protocol for high throughput T2K-TRAF2 heterodimer formation assay.
   A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P T2K protein 10×stock: $10^{-8}$–$10^{-6}$M "cold" T2K supplemented with 200,000–250,000 cpm of labeled T2K (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2mM $NaVo_3$ (Sigma # S-6508) in 10 ml of PBS.

TRAF2: $10^{-7}$–$10^{-5}$M biotinylated TRAF2 in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-T2K (20–25,000 cpm/0.1–10 pmoles/well= $10^{-9}$–$10^{-7}$M final conc).

Shake at 25° C. for 15 minutes.

Incubate additional 45 minutes at 25° C.

Add 40 μl biotinylated TRAF2 (0.1–10 pmoles/40 ul in assay buffer)
Incubate 1 hour at room temperature.
Stop the reaction by washing 4 times with 200 μM PBS.
Add 150 μM scintillation cocktail.
Count in Topcount.
D. Controls for all assays (located on each plate):
a. Non-specific binding
b. Soluble (non-biotinylated TRAF2) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated T2K protein comprising SEQ ID NO: 2 or a fragment thereof having T2K-specific activity.

2. An isolated protein according to claim 1, wherein said protein specifically phosphorylates IκB at serine 36.

3. An isolated protein according to claim 1, wherein said protein comprises a deletion mutant of SEQ ID NO:2, said deletion mutant comprising SEQ ID NO:2, residues 1–250 or 251–729.

4. A method of screening for an agent which modulates the binding of a T2K protein to a binding target, said method comprising the steps of:
   incubating a mixture comprising:
      an isolated protein according to claim 1,
      a binding target of said protein, and
      a candidate agent;
   under conditions whereby, but for the presence of said agent, said protein specifically binds said binding target at a reference affinity;
   detecting the binding affinity of said protein to said binding target to determine an agent-biased affinity,
   wherein a difference between the agent-biased affinity and the reference affinity indicates that said agent modulates the binding of said protein to said binding target.

5. A method according to claim 4, wherein said binding target is a substrate comprising IκB serine 36 and said binding affinity is detected as phosphorylation of said IκB serine 36.

6. A method of screening for an agent which modulates IκB phosphorylation by an IκB kinase specific for IκB serine 36, said method comprising the steps of:
   incubating a mixture comprising:
      an isolated IκB serine 36 specific kinase,
      a substrate comprising IκB serine 36, and
      a candidate agent;
   under conditions whereby, but for the presence of said agent, said kinase specifically phosphorylates said substrate at IκB serine 36 at a reference activity;
   detecting the phosphorylation of said substrate by said kinase to determine an agent-biased activity,
   wherein a difference between the agent-biased activity and the reference activity indicates that said agent modulates modulates IκB serine 36 phosphorylation.

7. A method according to claim 6, wherein said kinase comprises the sequence of KIAA0151 or SEQ ID NO: 2, or a fragment of either which specifically phosphorylates IκB at serine 36.

* * * * *